United States Patent [19]
Escuyer et al.

[11] Patent Number: 6,074,866
[45] Date of Patent: Jun. 13, 2000

[54] SHUTTLE VECTORS FOR THE INTRODUCTION OF DNA INTO MYCOBACTERIA AND UTILIZATION OF SUCH BACTERIA AS VACCINES

[75] Inventors: Vincent Escuyer, Massy; Alain Baulard, Tournai; Patrick Berche, Saint-Cloud; Camille Locht, Wannehain; Nadia Haddad, Paris, all of France

[73] Assignees: Institute National de la Santé et de la Recherche Medical (Inserm), Paris Cedex; Institut Pasteur de Lille, Lille Cedex, both of France

[21] Appl. No.: 08/737,588

[22] PCT Filed: May 19, 1995

[86] PCT No.: PCT/FR95/00664

§ 371 Date: Feb. 12, 1997

§ 102(e) Date: Feb. 12, 1997

[87] PCT Pub. No.: WO95/32296

PCT Pub. Date: Nov. 30, 1995

[30] Foreign Application Priority Data

May 20, 1994 [FR] France .................................. 94 06202

[51] Int. Cl.[7] ...................................................... C12N 1/20
[52] U.S. Cl. ............................................................ 435/252.3
[58] Field of Search ........................................... 435/252.3

[56] References Cited

FOREIGN PATENT DOCUMENTS

| 0521220 | 1/1993 | European Pat. Off. . |
|---|---|---|
| WO90/00594 | 1/1990 | WIPO . |
| WO90/10701 | 9/1990 | WIPO . |
| WO91/13157 | 9/1991 | WIPO . |

OTHER PUBLICATIONS

Steingrube et al., Antimicrobial Agents and Chemotherapy 35(5):819–823, 1991.
Aldovini et al., *Journal of Bacteriology*, vol. 175, No. 22, pp. 7282–7289 (1993).
Ranes et al., *Journal of Bacteriology*, vol. 172, No. 5, pp. 2793–2797 (1990).
Robinson and Tuovinen, *Microbiological Reviews*, vol. 48, No. 2, pp. 95–124 (1984).
Fellay et al., *Gene*, vol. 52, pp. 147–154 (1987).
Griffin et al., *Proceedings of the National Academy of Sciences USA*, vol. 84, pp. 3112–3116 (1987).
Silver and Walderhaug, *Microbiological Reviews*, vol. 56, No. 1 pp. 195–228 (1992).
Nies, *Plasmid* vol. 27, pp. 17–28 (1992).
Table of Contents from Maniatis et al., *Molecular Cloning: A Laboratory Manual.* (1982) Cold Spring Harbor Laboratory, Cold Spring Harbor, NY, USA.
Baulard et al., *Nucleic Acid Research*, vol. 20, p. 4105 (1992).
Snapper et al., *Molecular Microbiology*, vol. 4, pp. 1911–1919 (1990).
Journal of Bacteriology, vol. 172, Nov. 1990, pp. 6557–6567, Herrero, M. et al., "Transposon Vectors Containing Non–Antibiotic Resistance Selection Markers for Cloning and Stable Chromosomal Insertion of Foreign Genes in Gram–Negative Bacteria".
Journal of Bacteriology, vol. 157, Feb. 1984, pp. 669–672, Meissner, P.S. et al., "Plasmid–Encoded Mercuric Reductase in *Mycobacterium scrofulaceum*".
Proceedings of the National Academy of Sciences of USA, vol. 85, Sep. 1988, pp. 6987–6991, Snapper, S.B. et al., "Lysogeny and Transformation in Mycobacteria: Stable Expression of Foreign Genes".
Plasmid, vol. 27, No. 1, Jan. 1992, pp. 4–16, Misra, T.K., "Bacterial Resistances to Inorganic Mercury Salts and Organomercurials".
Plasmid, vol. 27, No. 1, Jan. 1992, pp. 29–40, Kaur, P. & Rosen, B., "Plasmid–Encoded Resistance to Arsenic and Antimony".
Microbiology, vol. 141, Part 4, pp. 1045–1050, Apr. 1995, Baulard, A. et al., "Mercury Resistance as a Selective Marker for Recombinant Mycobacteria".

*Primary Examiner*—Remy Yucel
*Attorney, Agent, or Firm*—Greenblum & Berstein, P.L.C.

[57] ABSTRACT

Shuttle vectors for inserting DNA in mycobacteria comprising at least one origin of functional replication in said mycobacteria, another origin of functional replication in other bacteria, an enzyme cutting site allowing the insertion of DNA coding for a protein capable of being expressed in the mycobacteria, characterized in that they also carry a gene providing on said mycobacteria resistance to a compound containing a heavy metal.

7 Claims, 9 Drawing Sheets ns6,074,866

SHUTTLE VECTORS FOR THE INTRODUCTION OF DNA INTO MYCOBACTERIA AND UTILIZATION OF SUCH BACTERIA AS VACCINES

The present application is a U.S. National Stage Application of PCT/FR95/00664 filed May 19, 1995.

FIELD OF THE INVENTION

This invention relates to shuttle vectors for inserting DNA in mycobacteria.

It also relates to the use as vaccines of these mycobacteria in which one of these vectors has been inserted.

BACKGROUND OF THE INVENTION

The Mycobacterium genus comprises over 50 species, including major pathogens for the human such as *Mycobacterium tuberculosis*, agent of tuberculosis, *Mycobacterium leprae*, agent of leprosy, and *Mycobacterium avium*, a major opportunist in the course of AIDS. Little is known of the genetic mechanisms of the virulence of *M. tuberculosis* and the other pathogenic species for the human, due to the low growth rate of these bacteria and the lack of adequate cloning vectors, and as a result it is difficult to insert foreign DNA in these microorganisms. Moreover, the mycobacteria show a particular resistance to many antibiotics due to the fact that the constitution of their wall is poorly permeable to these molecules. However, recent studies have shown that it is possible to introduce foreign DNA in BCG with a view to expressing antigens heterologous to this bacterium.

In the case of BCG manipulation, the use of markers of resistance to antibiotics hitherto available in mycobacteria such as the aph3 gene providing a high degree of resistance to kanamycin or genes providing resistance to streptomycin or spectinomycin, cannot be envisaged because it could cause a dissemination of resistance to these antibiotics in the environment in the event that recombinant BCG is used for therapeutic or prophylactic purposes in the human or the animal. It is thus of the utmost importance to be able to develop resistance markers which are harmless for the environment in order to select recombinant mycobacteria which can be widely used.

At the present time, only a very small number of markers usable in mycobacteria is available.

Thus, Aldovini et al. (J. Bacteriol, 1993, 175, 7282–7289) have isolated the gene coding for orotidine-5'-monophosphate decarboxylase (OMP-DCase) of *Mycobacterium bovis* BCG.

Another marker, the cI gene, coding for the L1 phage repressor, has also been used (patent application WO-90/00594).

Shuttle vectors based on these markers and allowing the transfer of DNA between *Escherichia coli* and Mycobacterium have already been described. Thus, patent application WO-91/13 157 describes two shuttle vectors, pEP2 and pEP3, respectively carriers of a gene of resistance to kanamycin and hygromycin.

One of these vectors, pEP2, is modified by the introduction of the protein promoter MBP70 of Mycobacterium, as described in patent application WO-90/10 701.

Other shuttle vectors usable in mycobacteria and carrying markers of resistance to antibiotics, auxotrophic markers or the cI gene have been described in patent application WO 90/00594.

Finally, Ranes et al. (J. Bacteriol. 1990, 172, 2793–2797) have described the construction of a shuttle vector called pRR3 carrying a gene of resistance to kanamycin expressing itself in *Mycobacterium bovis* BCG and *Mycobacterium smegmatis*.

A strain of non-pathogenic saprophytic mycobacterium resistant to mercury carrying a plasmid of 115 MD was also known (Meissner and Falkinham, J. Bacteriol, 157, 669–672, 1984). This very large plasmid was not, however, characterized. In particular, the genes involved in the resistance to mercury were neither localized nor identified, and consequently this plasmid could not be used as a shuttle plasmid. Moreover, saprophytic mycobacteria do not belong to pathogenic mycobacteria, the latter being principally included in the *M. tuberculosis*, *M. bovis* and *M. leprae* species.

The result was that those skilled in the art wishing to transfer DNA coding for antigens, obtained by cloning in *Escherichia coli*, to mycobacteria with a view to fabricating vaccines, was confronted with a lack of easy-to-manipulate vectors carrying markers expressing themselves in *E. coli* and mycobacteria, and without danger to human or animal health. The use of genes of resistance to antibiotics of therapeutic aim must, in fact, be ruled out for the reasons given above. The use of auxotrophic mutants gives rise to practical difficulties of selection and moreover involves the need to obtain mutants for each mycobacterium strain.

SUMMARY OF THE INVENTION

The applicants therefore set out to find other markers which could be included in shuttle vectors without excessively reducing the ability of said vectors to include other DNA fragments, and which would provide on the mycobacteria in which they are expressed characters making it possible to distinguish them, in a way which is both unambiguous and easy to implement, from mycobacteria not carrying these markers.

The applicants have thus surprisingly revealed that shuttle vectors originating from Gram-negative bacteria, carrying genes of resistance to a compound containing a heavy metal such as inorganic mercury or mercurial compounds, were expressed in Gram-positive bacteria and could be used for the transfer of DNA between *Escherichia coli* and Mycobacterium, and that bacteria carrying these shuttle vectors could be selected easily.

This invention therefore relates to a shuttle vector for inserting DNA in mycobacteria comprising at least one origin of functional replication in said mycobacteria, another origin of functional replication in other bacteria, such as *E. coli*, an enzyme cutting site allowing the insertion of DNA coding for a protein capable of being expressed in the mycobacteria, characterized in that it also carries a gene providing on said mycobacteria resistance to a compound containing a heavy metal such as inorganic mercury, a mercurial compound or arsenic.

It should be considered that those skilled in the art have for many years been confronted with the problem of seeking markers for the transfer of genes in mycobacteria, but that up to now no satisfactory solution has been found to this problem.

The solution found by the applicants, namely the choice of genes originating from Gram-negative bacteria and coding for a resistance to a heavy metal, is particularly surprising in view of the fact that those skilled in the art would not in theory have expected to find Gram-negative bacteria expressed in Gram-positive bacteria. Indeed, many studies have demonstrated the inability of genes from Gram-negative bacteria to express themselves in Gram-positive bacteria (Misra, Plasmid, 27, 4–16, 1992; Robinson and Tuovinen, Microbiological Reviews, Vol. 48 No. 2, 95–124, 1984).

The applicants have thus found a solution to a long-standing problem and one which, moreover, is of great importance to public health: mycobacteria and in particular *M. bovis* BCG, are considered as good candidates for vaccination against various diseases, provided that it is possible for these bacteria to express foreign antigens. This invention provides for an introduction of genes coding for these antigens which is both efficient and without danger to human health.

This invention therefore involves a major technical advance in the field of public health.

It should also be noticed that although markers of resistance to mercury were already known to exist, particularly in mycobacteria, those skilled in the art were in no way incited to integrate genes of resistance to mercury or mercurial compounds in shuttle vectors usable in mycobacteria. On the contrary, it is widely known that operons expressed for example in *E. coli* are not expressed in mycobacteria. Those skilled in the art were thus not incited to use in mycobacteria genes usually expressed in *E. coli*.

In other words, nothing suggested using genes of resistance, in particular to mercury or mercurial compounds, as genes of selection of mycobacteria having received the shuttle vectors.

While one of the aims of this invention relates to the transfer of heterologous DNA to Mycobacterium, it should be noted that the shuttle vectors may also be used for transferring DNA fragments of mycobacteria to other bacteria such as *Escherichia coli* in order to facilitate the genetic study of the mycobacteria. It is a fact that mycobacteria, largely due to their slow growth rate, are difficult to study from a genetic point of view, and this study is facilitated by the cloning of fragments of their DNA in *Escherichia coli*. The shuttle vectors concerned by this invention may also be advantageously used for cloning the DNA of mycobacteria and for the study of these bacteria.

They may also be used to attenuate the virulence of *M. tuberculosis* and other virulent mycobacteria with the assistance of transposons.

This invention should thus considerably hasten progress in the genetic analysis of mycobacteria and will permit the genetic manipulation of BCG in order to fabricate multivalent vaccines.

For the purposes of this invention, "heterologous DNA" is understood to mean DNA not belonging to the species of Mycobacterium chosen to express it. As examples of transferable heterologous DNA, those described in EP 91.401.601 will be cited.

The genes of resistance to mercury and other mercurial compounds such as organo-mercurial compounds, are organized in operons.

Six genes mer have been described up to now for the transportation of $Hg^{2+}$ ions in the cytoplasm and their detoxification.

The key enzyme is a mercuric reductase coded for the merA gene reducing the $Hg^{2+}$ ions to $Hg^0$ elemental mercury, a volatile compound of relatively little toxicity easily eliminated by the bacteria.

The gene merB is also known, a gene coding for an organo-mercurial lyase capable of splitting the C—Hg bond and of transforming the mercury in the $Hg^{2+}$ ion which is then detoxified by the mercuric reductase described above.

All the genes of resistance to mercury which may be used within the scope of this invention, together with their sequences, may be those listed in reviews by Misra (1992, cited above), by Robinson and Tuoniven (1984, cited above), Fellay et al. (1987, Gene, 52, 147–154), Griffin et al. (1987, Proc. Natl. Acad. Sci. USA, 84, 3112–3116) or Herrero et al. (1990, J. Bacteriol., 172, 6557–6567).

Any other gene of resistance to mercury expressing itself in the mycobacteria may, however, be integrated in the shuttle vectors concerned by this invention.

The vector concerned by this invention advantageously comprises either the gene merA on its own or the genes merA and merB, with the genes merT and merP.

In the former case, the vector advantageously comprises the merA operon of the transposon Tn501. In the latter case, the vector advantageously comprises the operons merA and merB cloned from the plasmid pDU1358 isolated from *Serratia marcescens* (Griffin et al., cited above) and expressing a wide spectrum of resistance to the $Hg^{2+}$ ion and to an organomercurial compound such as phenyl mercuric acetate (PMA).

Advantageously, a shuttle vector according to the invention and carrying the operon merA is the plasmid pMR001, filed with the Belgian Collections of Coordinated Microorganisms (BCCM) under No. LMBP 3046, and a vector carrying the two operons merA and merB is the plasmid pVN2 filed with the BCCM under No. LMBP 3047. These two plasmids also carry the genes merT and merP, as well as merR for the pMR001.

Although genes of resistance to mercury are advantageously used in this invention, it should nonetheless be noted that any other gene of resistance to a heavy metal such as arsenic, cadmium or lead may also be used.

Genes giving resistance to these other heavy metals are notably those described by Silver and Walderhaug (Microbiological Reviews, Vol. 56, No. 1, 195–228, 1992), Kaur and Rosen (Plasmid 27, 29–40, 1992) and Nies (Plasmid, 27, 17–28, 1992).

The gene ars may be used in order to provide resistance to arsenic. A vector carrying such a gene is pVN3, filed with the BCCM under No. LMPB 3048.

The gene(s) of resistance to the compound containing a heavy metal, as well as the enzyme cutting site, are preferentially carried by a transposon. Such a construction facilitates the integration of DNA carrying the cutting site in which has been inserted the DNA coding for the protein which it is desired to see expressed in the mycobacterium, particularly in cases when the homologous recombination is not very efficient.

As indicated above, said vector according to the invention comprises an enzyme cutting site allowing the insertion of DNA coding for a protein, capable of being expressed in the mycobacteria.

This invention thus relates not only to a vector having this cutting site but also to a vector in which a fragment of DNA coding for a protein heterologous to the chosen host has been inserted in this cutting site.

Such a protein is advantageously an antigen capable of inducing an immune response in the human or in the animal, such as an antigen of *M. leprae*, an antigen of *M. tuberculosis*, an antigen of the malaria vector, diphtheria toxoid, tetanus toxoid, an antigen of Leishmania, an antigen of a salmonella, an antigen of *M. africanum*, of *M. intracellulae*, of *M. avium*, an antigen of Treponema, of Toxoplasma, Schistosoma, Trypanosoma of Pertussis, an antigen of the herpes virus of HBV, of HCV, of Shigella, of Neisseria, of Borrelia, of the poliomyelitis virus, of the HIV virus, or an antigen of a venom of a snake, an insect or of *Vibrio cholerae* or any other antigen, including antigens coming from eukariotic cells, useful in immunoprophylaxis or immunotherapy.

The replication origins of the shuttle vector concerned by this invention are any origins allowing the replication of a vector in *E. coli* or in the mycobacteria. Advantageously, the replication origins in *E. coli* and in the mycobacteria are those used in the plasmid pRR3.

The origins of other plasmids such as pMSC262 and RSF1010 may also be advantageously used.

It should, however, be noted that if the origin is not functional in the mycobacteria, or if it is not optimally functional, the shuttle vector may integrate mycobacteria in the chromosomal DNA, for example by transposition or recombination.

The cutting site allowing the integration in the shuttle vector of the fragment of DNA coding for the protein which it is desired to express in the mycobacteria is any cutting site by a restriction enzyme making it possible to obtain sticky ends or blunt ends. Such an enzyme will be selected by those skilled in the art in the light of manipulation conditions such as ease of use of the enzyme.

Generally speaking, and particularly with reference to the production of the vector concerned by this invention and the integration of the DNA in this vector, those skilled in the art may refer to the following general technical manual: Maniatis et al. 1982, Molecular cloning: A Laboratory Manual; Cold Spring Harbor Laboratory, Cold Spring Harbor N.Y. USA or one of its recent re-editions.

Those skilled in the art may also refer to this manual for any matter concerning this invention.

This invention also relates to pathogenic mycobacteria, particularly *M. bovis, M. leprae, M. tuberculosis, M. avium, M. intracellulare* having a resistance to a compound containing a heavy metal such as inorganic mercury, a mercurial compound or arsenic.

In general, this invention relates to mycobacteria, in particular pathogenic or attenuated, carrying a vector such as described above.

It also relates to mycobacteria carrying a gene of resistance to a heavy metal and expressing a gene coding for a heterologous antigen.

"heterologous antigen" is understood as an antigen not usually found in the bacterium in which it is expressed.

The vector may be in the bacterium in a non-integrated form. However, it will be advantageously at least partly integrated in the bacterial chromosome.

It is especially advantageous for the mycobacteria to carry a transposon, containing the gene of resistance to the heavy metal and the gene coding for a protein capable of being expressed in the mycobacteria, inserted in their chromosome. Such a mode of application is particularly advantageous because it reduces the risks of loss of expression of the protein which may occur more frequently when the vectors are not integrated.

This invention also relates to pharmaceutical compositions containing at least one mycobacterium such as defined above in association with one or more compatible and pharmaceutically acceptable excipients and vaccines containing such mycobacteria.

Finally, this invention relates to a method of introducing a gene in a mycobacterium comprising at least one introduction step, in said mycobacterium, of a vector such as described above carrying said gene, and a step of selecting the mycobacteria in which the vector was introduced. The mycobacteria in which the plasmid has been introduced are advantageously selected for their resistance to mercury or a mercurial compound.

The vector is advantageously introduced in the mycobacteria by electroporation. However, any other method giving the same result may be used with equal success.

BRIEF DESCRIPTION OF THE DRAWINGS

This invention is illustrated, without in any way being limited, by the following examples in which:

In FIGS. 3 to 8 the growth of the clones is measured by the optical density at 600 nm (y-coordinate) in function of the concentration in PMA or $HgCl_2$ (x-coordinate).

DETAILED DESCRIPTION OF THE PREFERRED EMBODIMENT

EXAMPLES

Example 1

Construction of Shuttle Plasmids Carrying Genes of Resistance to Mercury pMR001 and pVN2 and Their Transfer to Mycobacteria Two plasmids carrying operons mer are used:

pHP45-Ω-Hg (Fellay et al. (1987, Gene, 52, 147–154)) containing the operon mer of the transposon Tn501 originally found in Pseudomonas aeruginosa and expressing solely resistance to inorganic mercury, coded by merA,.

pLOF-Hg (Herrero et al. (1990, J. Bacteriol, 172, 6557–6567)) containing genes of resistance to both mercury and organomercurial compounds, including merA and merB, cloned from the plasmid pDU1358, originally isolated from *Serratia marcescens*, and thus expressing a wide spectrum of resistance to $Hg^{2+}$ ions and organomercurial compounds such as phenyl mercuric acetate (PMA).

The mer operons of these plasmids are inserted separately in the shuttle vector pRR3.

The bacteria, *E. coli* or mycobacteria, used in this example are listed in Table 1.

1) Fabrication of pMR001

The 4.3 kb fragment SmaI of pH45ΩHg containing the mer operon of Tn501 is inserted in the single site ScaI of pRR3.

The mixture, after ligation, is used for transforming *E. coli* XL1-Blue by electroporation. The transformed bacteria are then spread on Luria Broth (LB) complemented with 12 µg/ml $HgCl_2$.

Several colonies expressing resistance to mercury appear after an incubation period of one night at 37° C., whereas no colony is observed when bacteria transformed with pRR3 alone are spread.

The plasmids of 10 clones having a resistance to mercury are extracted and analyzed. The presence of recombinant plasmids having the expected restriction plan is confirmed.

Figure 1:
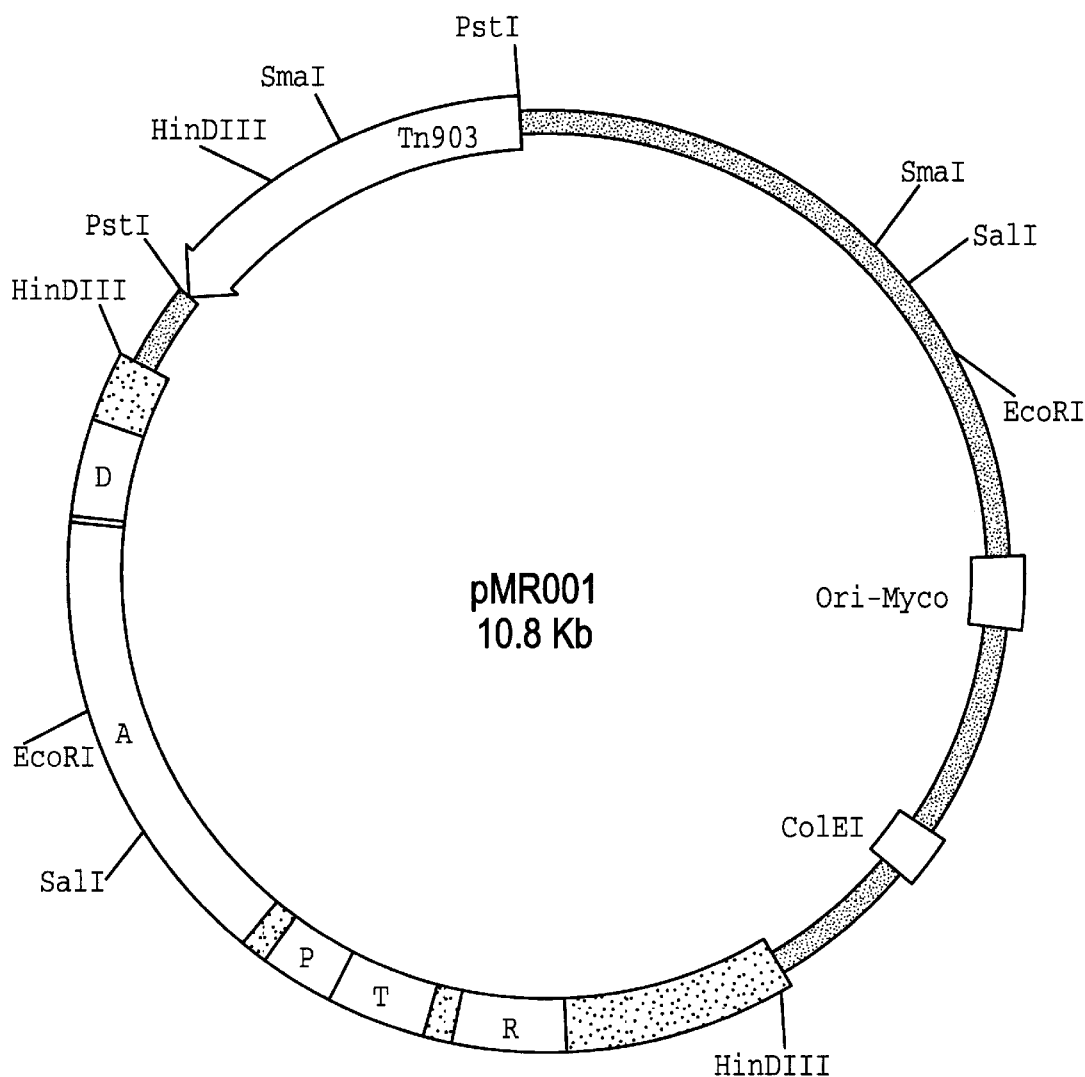
FIGS. 1 and 2 represent diagrammatic maps of plasmids pMR001 and pVN2.

A plasmid designated pMR001 and whose diagrammatic restriction map is represented in FIG. 1, is now used for transforming the mycobacteria.

2) Fabrication of pVN2

A similar strategy is used with pLOF-Hg, a plasmid carrying the mer operon of *S. marcescens*. The 3 kb fragment Mlu of pLOF-Hg carrying the mer operon of *S. marcescens* is treated by the DNA polymerase I (Klenow) and then inserted in the single site ScaI of pRR3. The transformed bacteria express the resistance to mercury, and no rearrangement in the recombined plasmids is observed.

A plasmid designated pVN2 was subsequently used for transforming the mycobacteria.

Figure 2:
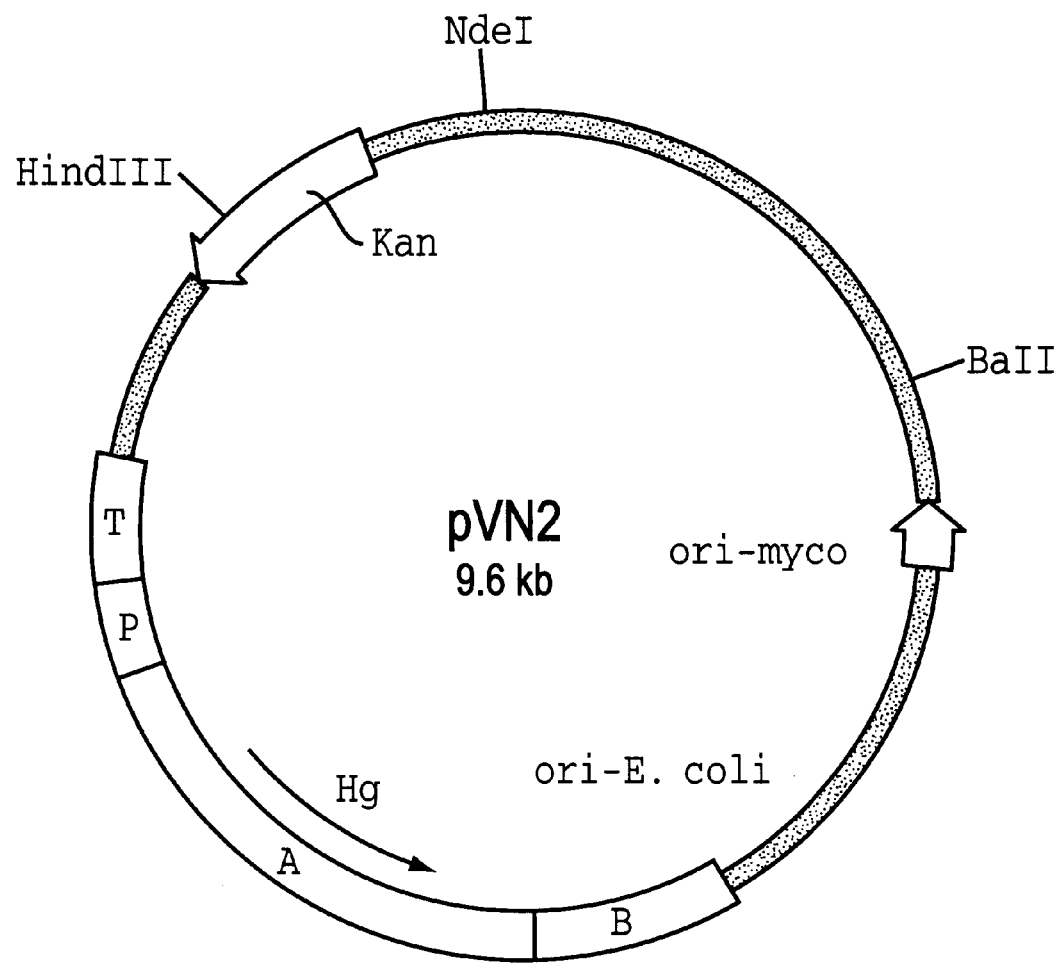
Figure 3:
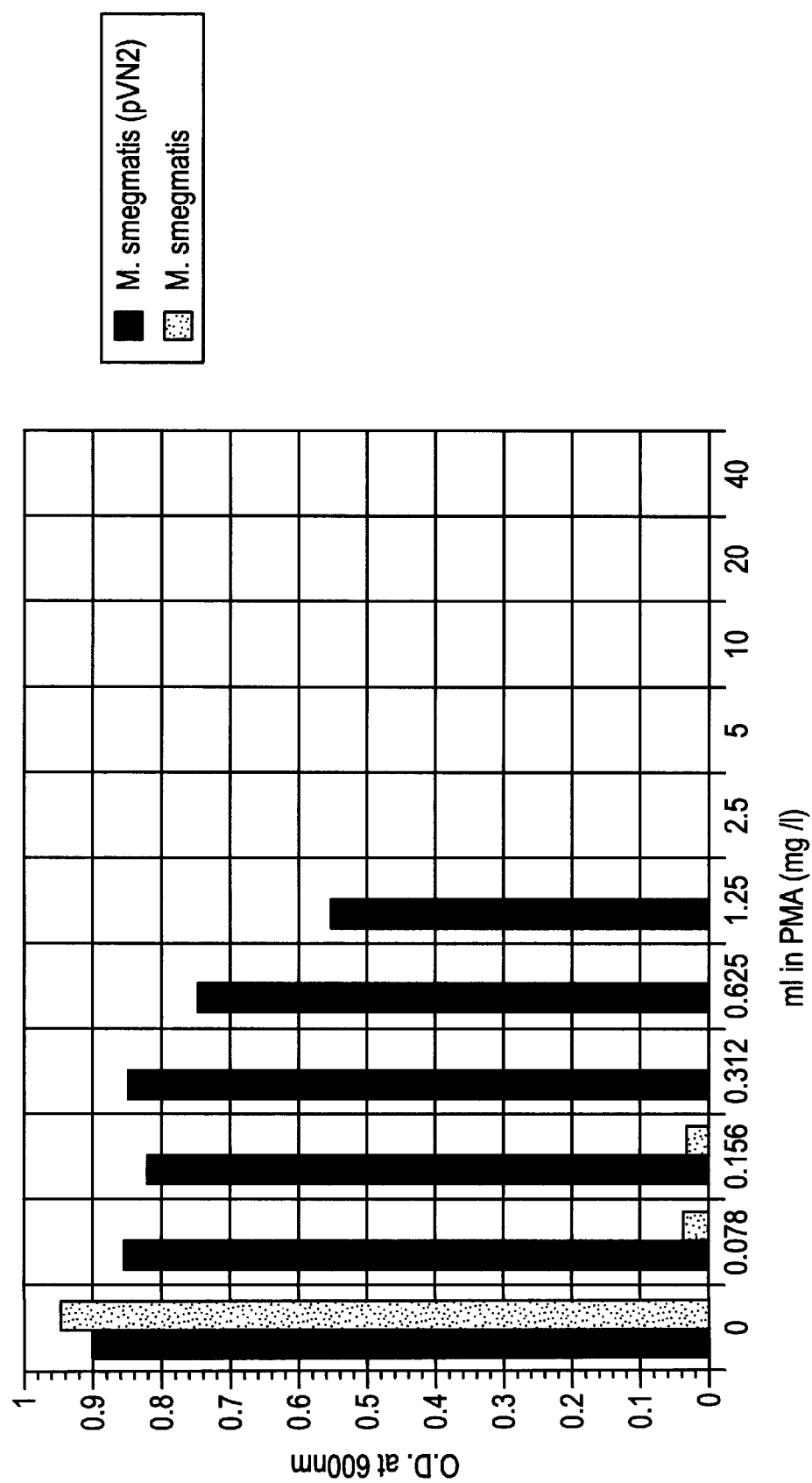
FIGS. 3 and 4 illustrate the sensitivity of recombinant and non-recombinant *M. smegmatis* clones respectively to PMA and $HgCl_2$.
Figure 4:
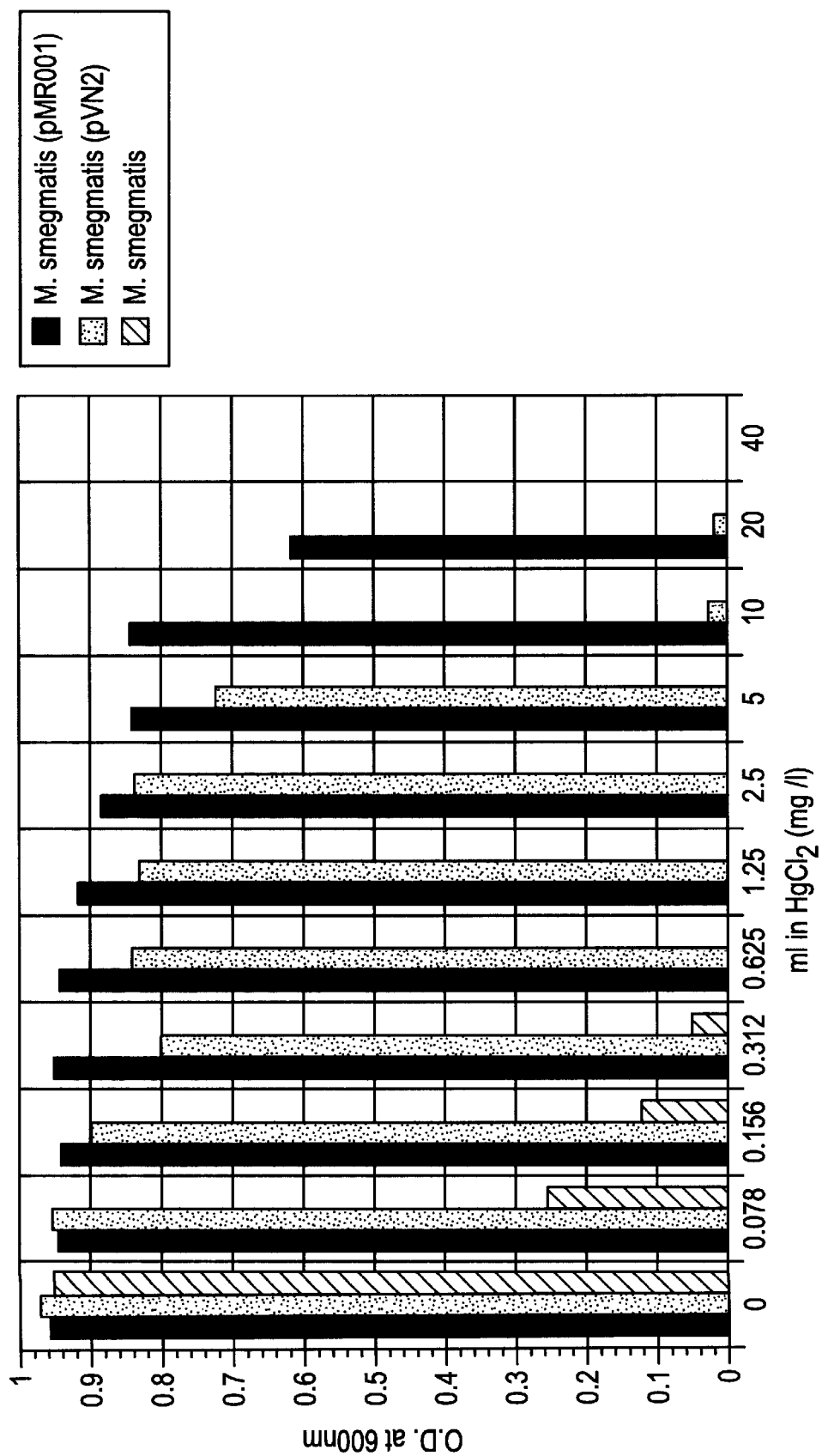
Figure 5:
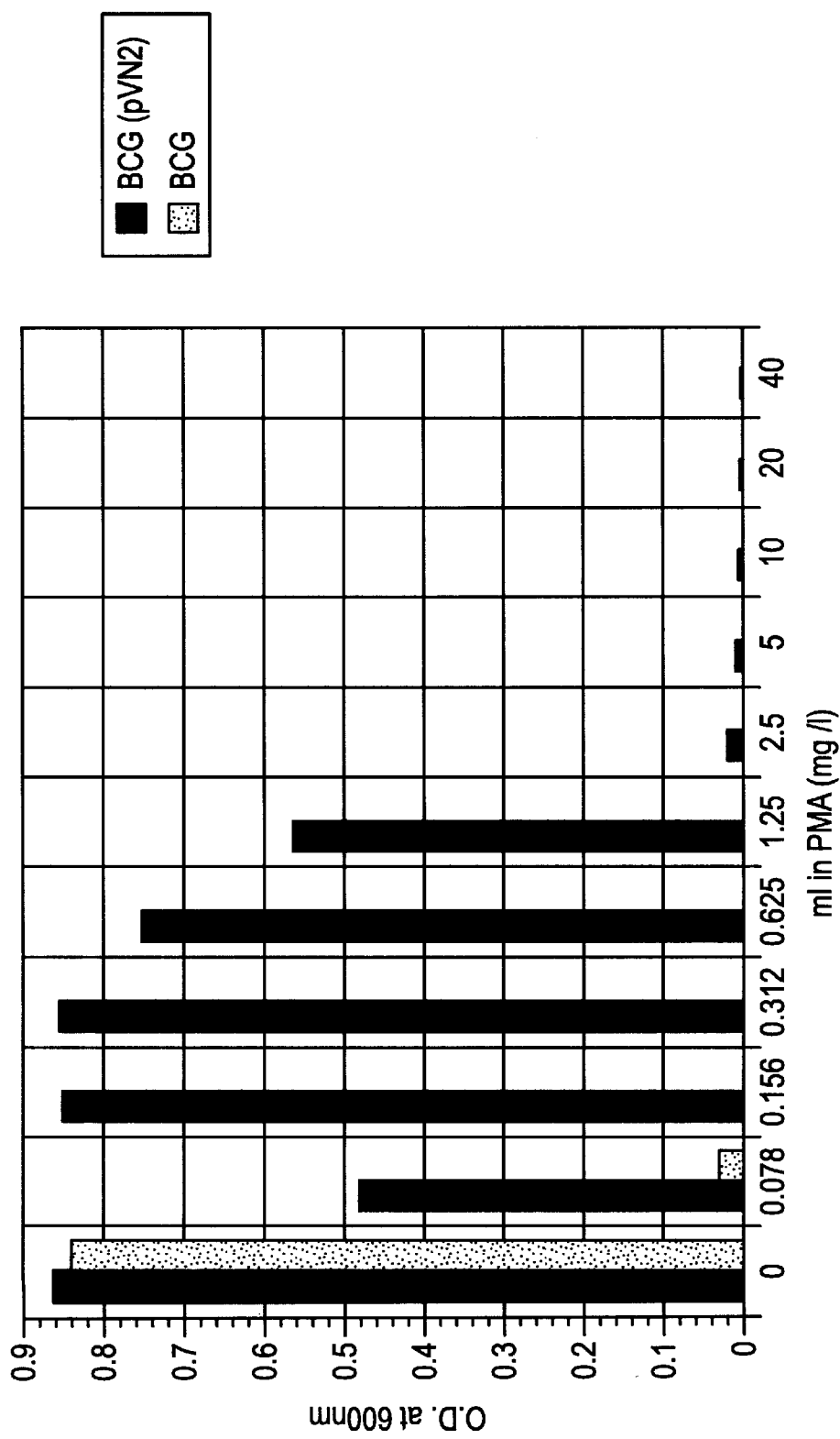
FIGS. 5 and 6 illustrate the sensitivity of recombinant and non-recombinant BCG clones respectively to PMA and $HgCl_2$.
Figure 6:
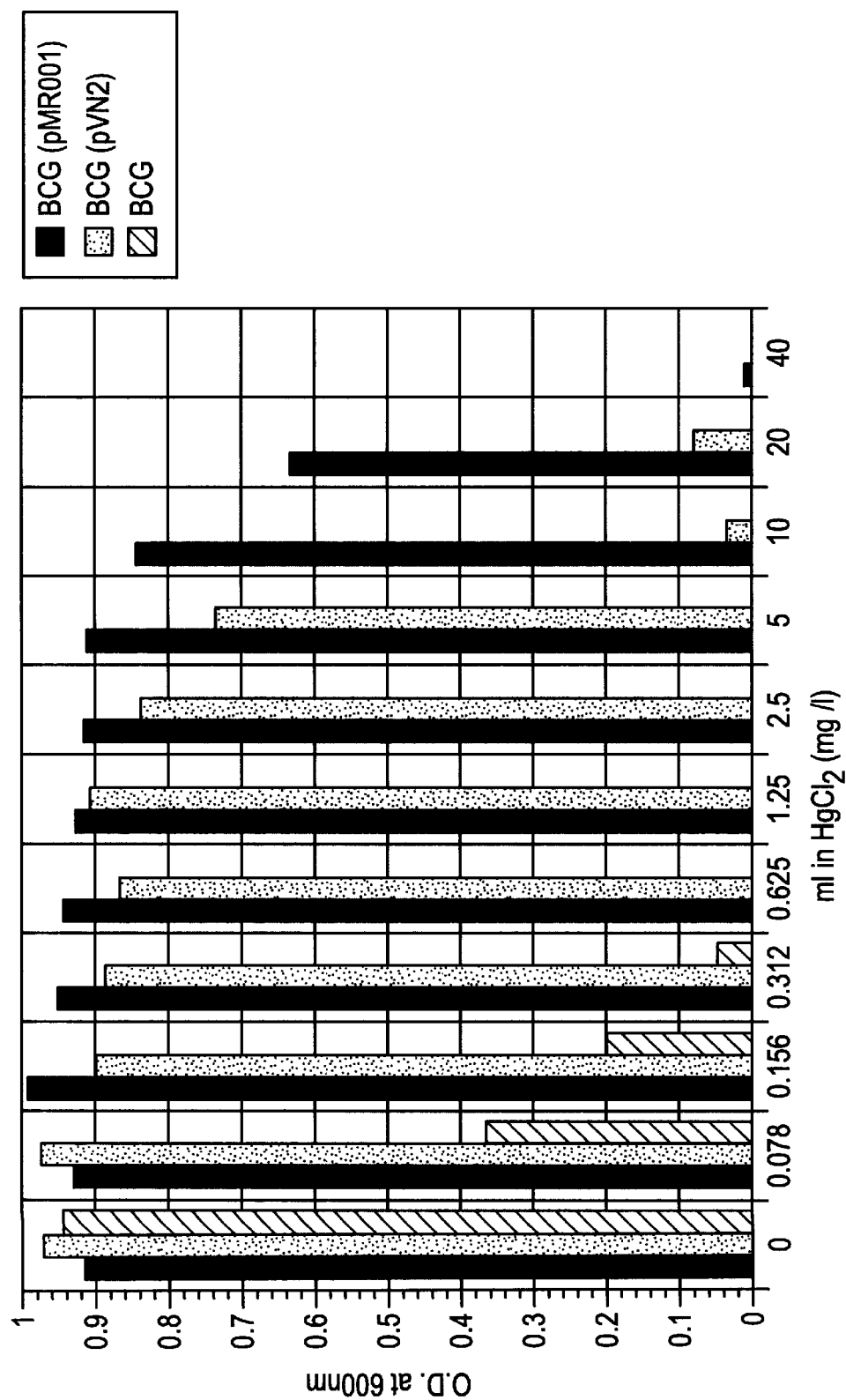
Figure 7:
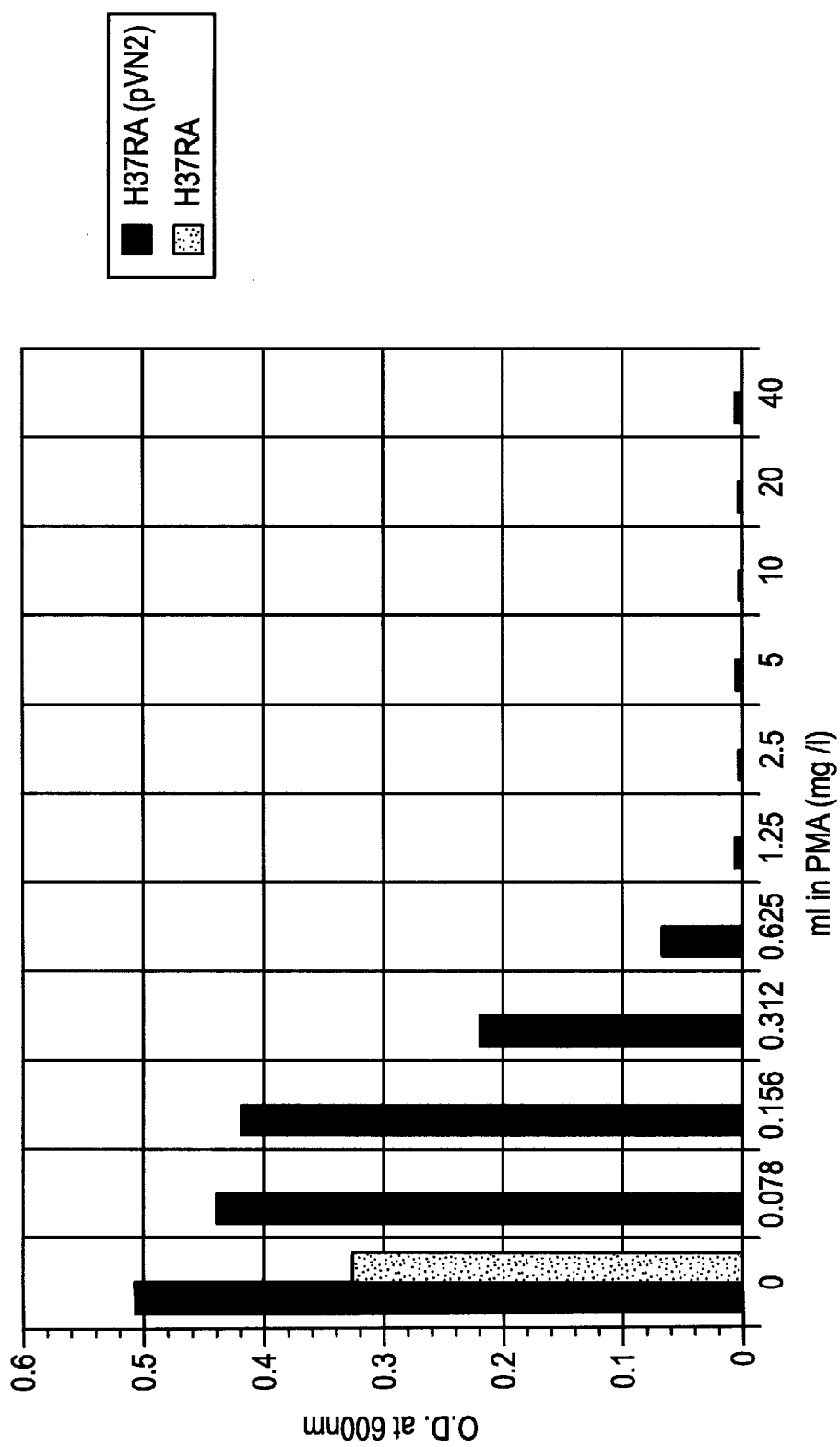
FIGS. 7 and 8 illustrate the sensitivity of recombinant or non-recombinant H37RA clones respectively to PMA and $HgCl_2$.
Figure 8:
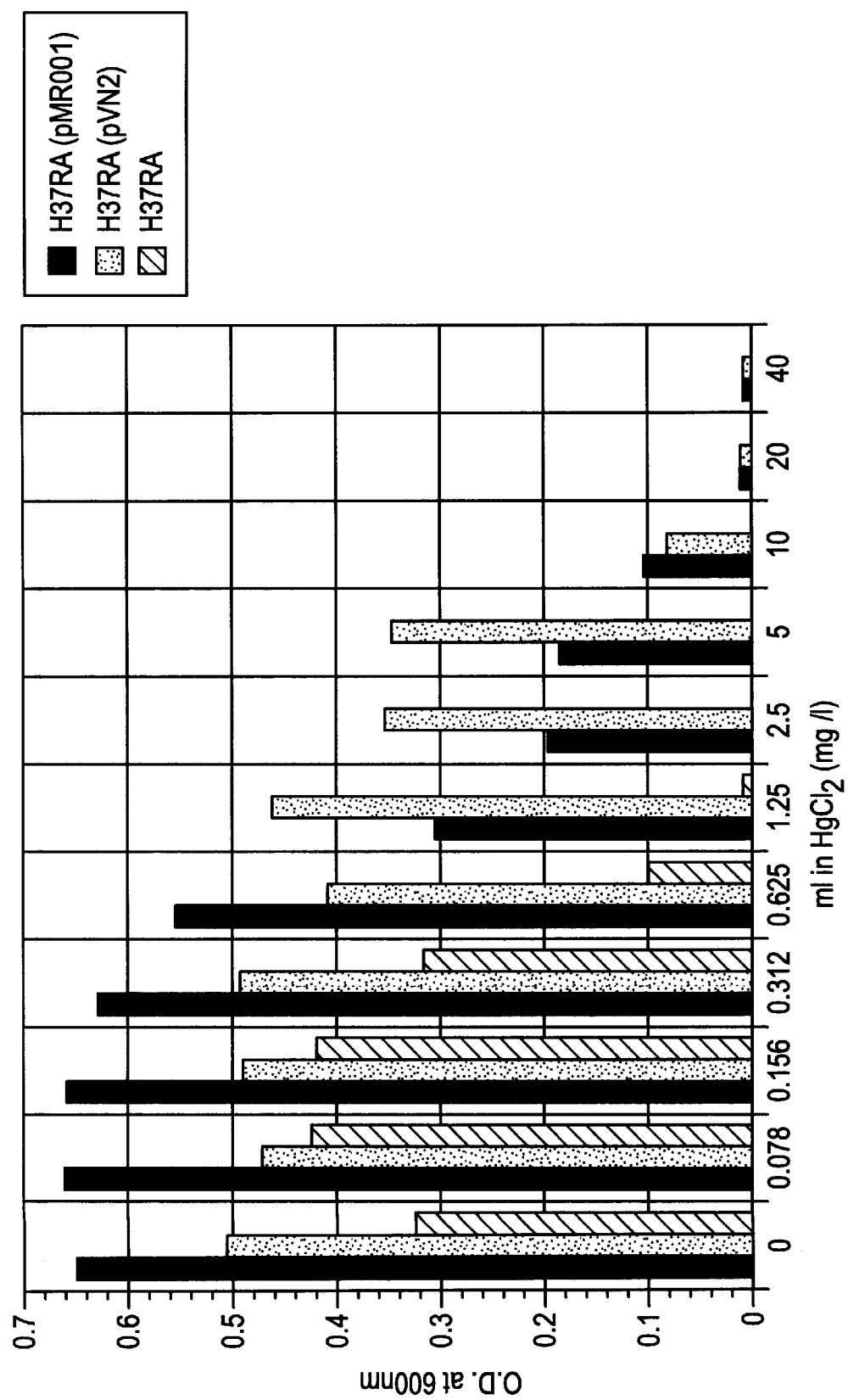

This plasmid is represented in diagram form in FIG. 2.

3) Electroporation of Mycobacteria by pMR001 and pVN2 pMR001 and pVN2, carrying resistance to mercury and resistance to kanamycin, were used for electrotransforming *M. smegmatis*, *M. bovis* BCG and *M. tuberculosis*, using an electroporation appliance (Eurogentec S. A.), such as described by Baulard et al. (1992, Nucleic Acid Research 20, 4105).

Since the transcription-translation signals of the mer operon of *P. aeruginosa* cannot be recognized in the mycobacteria, the bacteria transformed by pMR001 were first of all selected on Middlebrook agar 7H10 (Difco, Detroit, Mich., USA) complemented with kanamycin at the rate of 20 µg/ml.

After five days, or two or three weeks, of incubation at 37° C., depending on the receiving mycobacterium, isolated recombinant colonies are obtained with the three species of mycobacteria.

In order to estimate the minimum inhibitory concentration (MIC), defined as the weakest concentration of mercurial compounds at which no bacterial growth is observed, 10 µl of a suspension of bacteria ($10^8$–$10^9$ bacteria/ml) are deposited in drops on Middlebrook agar medium 7H10 (Difco) or 100 µl are inoculated in Roux Middlebrook phials containing 10 ml of Sauton liquid medium complemented with increasing concentrations of $HgCl_2$.

The cultures are incubated at 37° C. for five days (*M. smegmatis*) or two to three weeks (*M. tuberculosis, M. bovis* BCG), until the bacterial growth is detectable in the control cultures.

Whereas the control mycobacteria show considerable susceptibility to concentrations of 0.15 µg/ml of $HgCl_2$ on solid medium, the mycobacteria carrying the plasmid pMR001 show a very marked increase in the level of the resistance to $HgCl_2$.

Complete inhibition of bacterial growth is observed only at concentrations of 160 µg/ml on solid medium. When the minimum inhibiting concentration (MIC) for $HgCl_2$ is determined in Sauton liquid medium, complete inhibition of bacterial growth is observed at a concentration of 1 µg/ml of $HgCl_2$ for the non-transformed control mycobacteria (Table 2).

In contrast, the mycobacteria carrying the plasmid pMR001 are still capable of growing at a concentration of 20 µg/ml of $HgCl_2$.

The plasmid DNA of 12 clones resisting to 15 µg/ml of $HgCl_2$ of three mycobacteria of different species, are then transferred by electroduction to bacteria *E. coli* XL1-Blue as described by Baulard (1992, cited above).

The transformed plasmids of *E. coli* resistant to mercury show a normal digestion plan.

As expected, the resistance to mercury provided by the plasmid pMR001 is restricted to inorganic mercury and does not concern the organomercurial compounds.

In order to determine whether the resistances to mercury of pMR001 and pVN2 can be used as direct selection markers for transforming mycobacteria, *M. bovis* BCG, *M. smegmatis* and *M. tuberculosis* mycobacteria electroporated with one of the two plasmids were directly spread on an agar medium 7H10 complemented with 12 µg/ml of $HgCl_2$. After 5 to 15 days of culture, depending on the species, $10^3$ resisting colonies per µg of pMR001 were obtained.

The same operations are carried out with the plasmid pVN2 expressing the resistance to inorganic mercury and to organomercurial compounds (PMA). The MIC of the non-transformed *M. smegmatis, M. bovis* BCG and *M. tuberculosis* is less than 0.15 µg/ml for PMA. The pVN2-carrying mycobacteria obtained by electroporation as described above grow on a agar medium 7H10 up to concentrations of 40 µg/ml of $HgCl_2$ and 5 µg/ml of PMA. $10^3$ resistant colonies per pg appear after 25 days on the agar boxes 7H10 containing 10 µg/ml of PMA.

In Sauton liquid medium, growth inhibition is observed at a concentration of 0.15 µg/ml of PMA for the non-transformed bacteria of the three species of mycobacteria.

The level of resistance to mercury for the mycobacteria transformed by pVN2 is estimated at 5 µg/ml of PMA or 40 mg/ml of $HgCl_2$ (Table 2).

The results obtained are summarized in FIGS. 3 to 8.

In all cases, a return transformation of *Escherichia coli* by electroduction confirms the presence of the expected plasmid in the clones of resistant mycobacteria.

Example 2

Construction of a Shuttle Vector Carrying Resistance to Arsenic

The plasmid pLOF/As carries the genes arsA and arsB originating from the plasmid pR773 which was isolated in various enterobacteria. The two genes are placed under the control of the aerobactine promoter.

A 3.4 kb fragment was obtained by digestion of pLof-As by the enzyme MluI, which carries arsA, arsB and the aerobactine promoter. The extremities of this fragment were filled with the DNA polymerase I, and the fragment was then cloned to the single site ScaI of the shuttle-vector *Escherichia coli*-mycobacterium pYUB12. The construction of this vector is described in Snapper et al. (PNAS, 1988, 85: 6987–6991; and Mol. Microbiol., 1990, 4: 1911–1919).

The plasmid pVN3 provides on *Mycobacterium smegmatis* a resistance to arsenic nitrate ($AsNO_3$) of the order of 10 mg/l.

Figure 9:
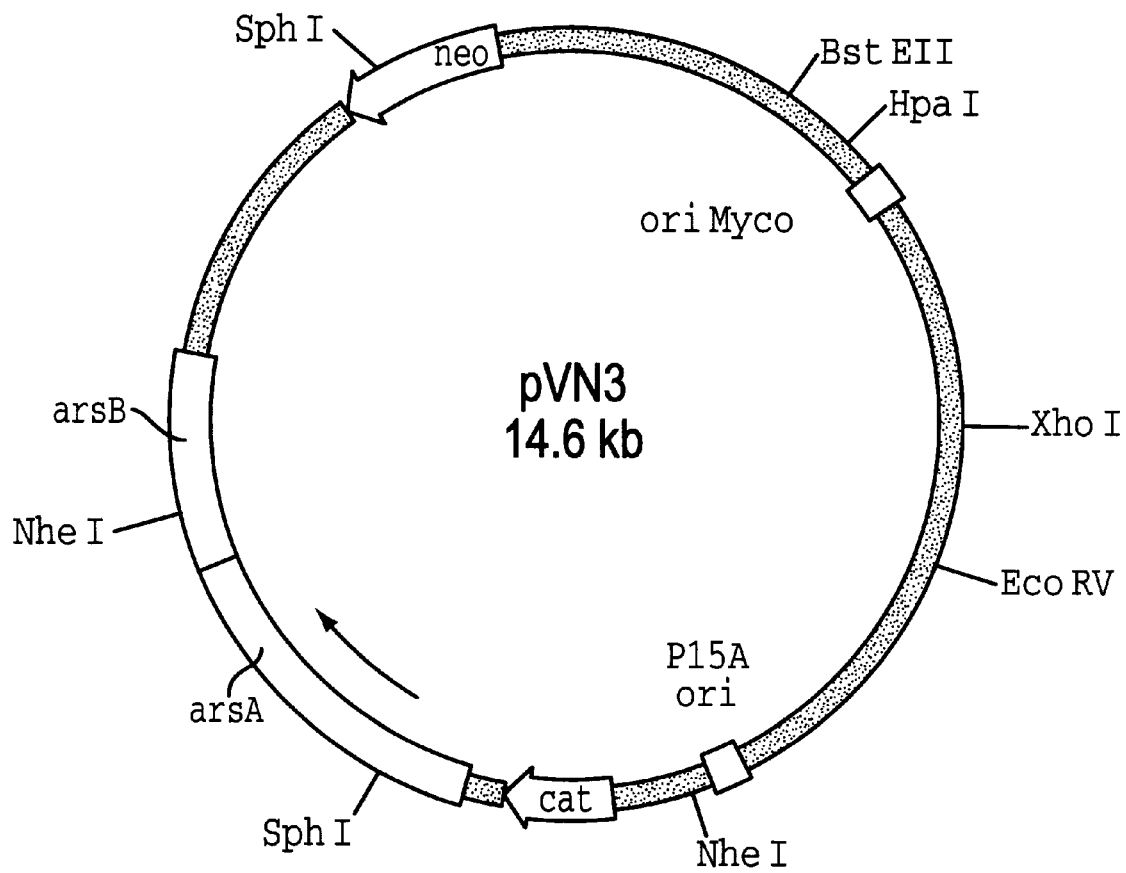
FIG. 9 is a diagrammatic map of plasmid pVN3.

This plasmid is represented in diagram form in FIG. 9.

Conclusion

The results obtained show that vectors expressing resistance to the heavy metals mercury and arsenic may be used as selection markers for recombinant mycobacteria.

The shuttle vectors concerned by this invention therefore allow a transfer which is at once efficient, easy to use and easy to select, of heterologous genes in host mycobacteria capable of expressing said heterologous genes.

TABLE 1

Bacteria and plasmids

| Bacteria and plasmids | Characteristics | Reference or origin |
|---|---|---|
| Strains *E. coli* XL-Blue | F':: Tn10proA$^+$B$^+$lac1$^g$D (lacZ) M15/recA1 and AlgyrA96 (Na1$^R$) thi hod R17 rk$^-$ mk$^+$) sup E44 rela 1 lac | New England Biolabs |
| Mycobacterium smegmatis mc$^2$ 155 | hypertransformable mutant derivated from mc$^2$6 wild-type strain | Snapper et al. (1990, Mol. Microbiol, 4, 1911–1919) |
| Mycobacterium bovis BCG 1173 P2 | | DMS Stockholm |
| Mycobacterium tuberculosis H37 Ra | avirulent mutant | National Collection of Cultures and Micro-organisms, Institut Pasteur |
| Plasmids | shuttle vector *E. coli*-mycobacterium | |
| pRR3 | Ap$^r$ Km$^r$, pAL5000 ori, pUC18 ori | Ranes et al (1990, J. Bacteriol, 172, 2793–2797) |
| pHP45Ω-Hg | merA$^+$ Tn50 (*P.aeruginosa*) | Fellay et al. (1987, Gene, 52, 147–154) |
| pLOF-Hg | Ap$^R$ Tn10 Hg$^r$ (merA, merB, merT, merP, IS10$^R$) | Herrero et al. (1990, J. Bacteriol, 172, 6557–6567) |

TABLE 2

Expression of resistance to mercury in mycobacteria carrying the pVN2 and pMR001 shuttle vectors

| | | MIC (mg/L)[2] | | |
|---|---|---|---|---|
| Mycobacterium[1] | Mercurial compounds | Solid medium | Liquid medium | Phenotypes[3] of resistance to mercury |
| Controls | $HgCl_2$ | 0.15 | 1.25 | S |
| | PMA | 0.15 | 0.15 | S |
| pMR001 | $HgCl_2$ | 160 | 40 | R |
| | PMA | 0.6 | ND | S |
| pVN2 | $HgCl_2$ | 160 | 40 | R |
| | PMA | 40 | 5 | R |

[1]The levels of resistance to mercury in *M. tuberculosis, M. smegmatis* and *M. bovis* BCG are equivalent.
[2]Minimum inhibiting concentrations (MIC) in Sauton liquid medium or Middlebrook agar medium 7H10
[3]S = Sensitive; R = Resistant to 12 μg/ml $HgCl_2$ or 10 μg/ml PMA.
ND = Not Determined

What is claimed is:

1. A recombinant pathogenic or attenuated mycobacterium transformed with nucleic acid, wherein the transformation imparts to the mycobacterium resistance to a compound containing a heavy metal.

2. The mycobacterium of claim 1, wherein the heavy metal comprises a member selected from the group consisting of inorganic mercury, a mercurial compound, arsenic, and mixtures thereof.

3. A mycobacterium which carries a vector, the vector comprising at least one origin of functional replication in said mycobacteria, another origin of functional replication in other bacteria, an enzyme cutting site allowing insertion of DNA coding for a protein capable of being expressed in the mycobacteria, wherein the vector also carries a gene providing on said mycobacteria, resistance to a compound containing a heavy metal.

4. A mycobacterium according to claim 3, wherein the mycobacterium is a pathogenic mycobacterium.

5. A mycobacterium according to claim 3, wherein the mycobacterium is a *Mycobacterium bovis* BCG, *M. smegmatis* or *M. tuberculosis.*

6. A mycobacterium which carries in its chromosome a transposon comprising (1) at least one gene coding for resistance to a compound containing a heavy metal, and (2) a gene coding for an antigen.

7. The mycobacterium of claim 6, wherein the heavy metal comprises a member selected from the group consisting of inorganic mercury, a mercurial compound, and mixtures thereof.

* * * * *